US00PP23229P2

(12) United States Plant Patent
Sakazaki

(10) Patent No.: US PP23,229 P2
(45) Date of Patent: Nov. 27, 2012

(54) ***CALIBRACHOA* PLANT NAMED 'USCAL88203'**

(50) Latin Name: ***Calibrachoa* sp.**
Varietal Denomination: USCAL88203

(75) Inventor: Ushio Sakazaki, Shiga (JP)

(73) Assignee: Plant 21 LLC, Bonsall, CA (US)

( * ) Notice: Subject to any disclaimer, the term of this patent is extended or adjusted under 35 U.S.C. 154(b) by 0 days.

(21) Appl. No.: 13/135,602

(22) Filed: Jul. 8, 2011

(51) Int. Cl.
*A01H 5/00* (2006.01)

(52) U.S. Cl. ..... Plt./413

(58) Field of Classification Search ..... Plt./413
See application file for complete search history.

*Primary Examiner* — Annette Para
(74) *Attorney, Agent, or Firm* — C. A. Whealy

(57) ABSTRACT

A new and distinct cultivar of *Calibrachoa* plant named 'USCAL88203', characterized by its compact, outwardly spreading and mounding plant habit; freely branching growth habit; dense and bushy appearance; early and freely flowering habit; yellow orange-colored flowers with random red-colored flecks and streaks; and good garden performance.

1 Drawing Sheet

Botanical designation: *Calibrachoa* sp.
Cultivar denomination: 'USCAL88203'.

BACKGROUND OF THE INVENTION

The present invention relates to a new and distinct cultivar of *Calibrachoa* plant, botanically known as *Calibrachoa* sp. and hereinafter referred to by the name 'USCAL88203'.

The new *Calibrachoa* plant is a product of a planned breeding program conducted by the Inventor in Higashiomi, Shiga, Japan and Bonsall, Calif. The objective of the breeding program is to create new *Calibrachoa* plants with uniform plant habit, freely branching growth habit, unique flower coloration and good garden performance.

The new *Calibrachoa* plant originated from a cross-pollination made by the Inventor on May 7, 2008 in Higashiomi, Shiga, Japan of a proprietary seedling selection of *Calibrachoa* sp. identified as code name CJ0702-01, not patented, as the female, or seed, parent with *Calibrachoa* sp. 'Suncalsifopi', disclosed in U.S. Plant Pat. No. 20,856, as the male, or pollen, parent. The new *Calibrachoa* plant was discovered and selected by the Inventor as a single flowering plant within the progeny of the stated cross-pollination in a controlled environment in Bonsall, Calif. on May 27, 2009.

Asexual reproduction of the new *Calibrachoa* plant by terminal cuttings in a controlled environment in Bonsall, Calif. since May 28, 2009 has shown that the unique features of this new *Calibrachoa* plant are stable and reproduced true to type in successive generations.

SUMMARY OF THE INVENTION

Plants of the new *Calibrachoa* have not been observed under all possible environmental conditions and various cultural practices. The phenotype may vary somewhat with variations in environmental conditions such as temperature and light intensity without, however, any variance in genotype.

The following traits have been repeatedly observed and are determined to be the unique characteristics of 'USCAL88203'. These characteristics in combination distinguish 'USCAL88203' as a new and distinct *Calibrachoa* plant:

1. Compact, outwardly spreading and mounding plant habit.
2. Freely branching growth habit; dense and bushy appearance.
3. Early and freely flowering habit.
4. Yellow orange-colored flowers with random red-colored flecks and streaks.
5. Good garden performance.

The new *Calibrachoa* plant can be compared to plants of the female parent selection. Plants of the new *Calibrachoa* differ primarily from plants of the female parent selection in flower color as plants of the female parent selection have dark cherry pink-colored flowers. In addition, plants of the new *Calibrachoa* are more compact and mounding than plants of the female parent selection.

The new *Calibrachoa* plant can be compared to plants of the male parent, 'Suncalsifopi'. Plants of the new *Calibrachoa* differ primarily from plants of 'Suncalsifopi' in flower color as plants of 'Suncalsifopi' have pale pink-colored flowers. In addition, plants of the new *Calibrachoa* are more compact than plants of 'Suncalsifopi'.

Plants of the new *Calibrachoa* can be compared to plants of the *Calibrachoa* 'USCALI53M', disclosed in U.S. Plant Pat. No. 17,680. In side-by-side comparisons conducted in Bonsall, Calif., plants of the new *Calibrachoa* differed primarily from plants of 'USCALI53M' in the following characteristics:

1. Plants of the new *Calibrachoa* were more compact and mounding than plants of 'USCALI53M'.
2. Plants of the new *Calibrachoa* and 'USCALI53M' differed in flower color as plants of 'USCALI53M' had yellow and dark red bi-colored flowers.

BRIEF DESCRIPTION OF THE PHOTOGRAPHS

The accompanying colored photographs illustrate the overall appearance of the new *Calibrachoa* plant showing the colors as true as it is reasonably possible to obtain in colored reproductions of this type. Colors in the photographs may differ slightly from the color values cited in the detailed botanical description which accurately describe the colors of the new *Calibrachoa* plant.

The photograph at the bottom of the sheet comprises a side perspective view of a typical flowering plant of 'USCAL88203' grown in a container.

The photograph at the top of the sheet comprises a close-up of a typical flowering plant of 'USCAL88203'.

DETAILED BOTANICAL DESCRIPTION

The aforementioned photographs and following observations, measurements and values describe plants grown during the late spring and early summer in 15-cm containers in a polyethylene-covered greenhouse in Bonsall, Calif. During the production of the plants, day temperatures averaged 24° C., night temperatures averaged 18° C. and light levels averaged 7,000 foot-candles. Plants were pinched one time and were seven weeks old when the photographs and description were taken. In the following description, color references are made to The Royal Horticultural Society Colour Chart, 2007 Edition, except where general terms of ordinary dictionary significance are used.

Botanical classification: *Calibrachoa* sp. 'USCAL88203'.

Parentage:

*Female, or seed, parent*.—Proprietary seedling selection of *Calibrachoa* sp. identified as code name CJ0702-01, not patented.

*Male, or pollen, parent*.—*Calibrachoa* sp. 'Suncalsifopi', disclosed in U.S. Plant Pat. No. 20,856.

Propagation:

*Type*.—By terminal cuttings.

*Time to initiate roots, summer*.—About four days at temperatures ranging from 17° C. to 29° C.

*Time to initiate roots, winter*.—About six days at temperatures ranging from 17° C. to 21° C.

*Time to produce a rooted plant, summer*.—About 22 days at temperatures ranging from 17° C. to 29° C.

*Time to produce a rooted plant, winter*.—About 25 days at temperatures ranging from 17° C. to 21° C.

*Root description*.—Medium in thickness, fibrous; white in color.

*Rooting habit*.—Freely branching; medium density.

Plant description:

*Plant and growth habit*.—Compact, outwardly spreading and mounding plant habit; freely branching habit with about seven primary lateral branches each with multiple secondary lateral branches; pinching enhances branching; moderately vigorous, dense and bushy growth habit.

*Plant height*.—About 11 cm.

*Plant diameter*.—About 39 cm.

Lateral branch description:

*Length*.—About 16 cm.

*Diameter*.—About 2 mm.

*Internode length, vegetative*.—About 1.1 cm.

*Internode length, reproductive*.—About 2 cm.

*Strength*.—Strong.

*Aspect*.—Outwardly spreading to trailing.

*Texture*.—Pubescent.

*Color*.—Close to 146B.

Foliage description:

*Arrangement*.—Before flowering, alternate; after flowering, opposite; leaves simple.

*Length*.—About 2.8 cm.

*Width*.—About 1.2 cm.

*Shape*.—Oblanceolate.

*Apex*.—Rounded.

*Base*.—Attenuate.

*Margin*.—Entire.

*Texture, upper and lower surfaces*.—Pubescent.

*Venation pattern*.—Pinnate; arcuate.

*Color*.—Developing leaves, upper surface: Close to 137A. Developing leaves, lower surface: Close to 146B. Fully expanded leaves, upper surface: Close to N137A; venation, close to 137B. Fully expanded leaves, lower surface: Close to 147B; venation, close to 147C.

*Petiole*.—Length: About 2.5 mm. Diameter: About 2 mm. Texture, upper and lower surfaces: Pubescent. Color, upper surface: Close to 137C. Color, lower surface: Close to 147C.

Flower description:

*Flower arrangement and habit*.—Single salverform flowers arising from leaf axils; freely flowering habit with usually about 34 open flowers and flower buds per lateral branch; flowers face upright and outwardly.

*Fragrance*.—None detected.

*Natural flowering season*.—Early flowering habit, plants of the new *Calibrachoa* begin flowering about six weeks after planting; plants flower continuously from spring though the autumn in California.

*Flower longevity*.—Individual flowers last about five days on the plant; flowers persistent.

*Flower diameter*.—About 2.4 cm.

*Flower length* (*height*).—About 2.5 cm.

*Flower throat diameter*.—About 4 mm by 6 mm.

*Flower tube length*.—About 1.5 cm.

*Flower tube diameter, base*.—About 2 mm.

*Flower bud*.—Shape: Elongated oblong. Length: About 2.1 cm. Diameter: About 7 mm. Color: Close to 179C.

*Corolla*.—Arrangement: Five petals fused at the base and opening into a flared trumpet. Petal lobe length (from throat): About 1 cm. Petal lobe width: About 1.2 cm. Petal shape: Roughly obovate. Petal apex: Rounded. Petal margin: Entire. Petal texture, upper surface: Smooth, glabrous; velvety. Petal texture, lower surface: Pubescent. Throat texture: Smooth, glabrous. Tube texture: Pubescent. Color: Petal lobe, when opening, upper surface: Close to 22A; random flecks and streaks, close to 42A to 42B. Petal lobe, when opening, lower surface: Close to 31C with tints of close to 182C. Petal lobe, fully opened, upper surface: Close to 23B; random flecks and streaks, close to 45C and 42B; with development, primary color becoming closer to 23B to 23C and flecks/streaks, close to 42D; venation, close to 153A. Petal lobe, fully opened, lower surface: Close to 182C; venation, close to 147B. Throat: Close to 153D; venation, close to 152C. Tube: Close to 145C; venation, close to 152A.

*Calyx*.—Arrangement: One star-shaped calyx tube with five sepals in a single whorl and fused at the base. Sepal length: About 9 mm. Sepal width: About 2.5 mm. Sepal shape: Ligulate to narrowly elliptical. Sepal apex: Acute. Sepal margin: Entire. Sepal texture, upper and lower surfaces: Pubescent. Color, upper and lower surfaces: Close to 137A.

*Peduncles*.—Length: About 1.7 cm. Diameter: About 1 mm. Angle: About 30° to 45° from stem axis. Strength: Strong. Texture: Pubescent. Color: Close to 146C.

*Reproductive organs*.—Stamens: Quantity: About five per flower. Filament length: About 8 mm. Filament color: Close to 145D. Anther shape: Oval. Anther length: About 1 mm. Anther color: Close to 11A. Pollen amount: Scarce. Pollen color: Close to 12A. Pistils: Quantity: One per flower. Pistil length: About 1 cm. Style length: About 8 mm. Style color: Close to 144D. Stigma shape: Oval. Stigma color: Close to 144A. Ovary color: Close to 145C. Seeds and fruits: Seed and fruit development have not been observed on plants of the new *Calibrachoa*.

Garden performance: Plants of the new *Calibrachoa* have been observed to have good garden performance and tolerate wind, rain and temperatures ranging from about 1° C. to about 40° C.

Pathogen/pest resistance: Plants of the new *Calibrachoa* have not been observed to be resistant to pathogens and pests common to *Calibrachoa*.

It is claimed:

1. A new and distinct *Calibrachoa* plant named 'USCAL88203' as illustrated and described.

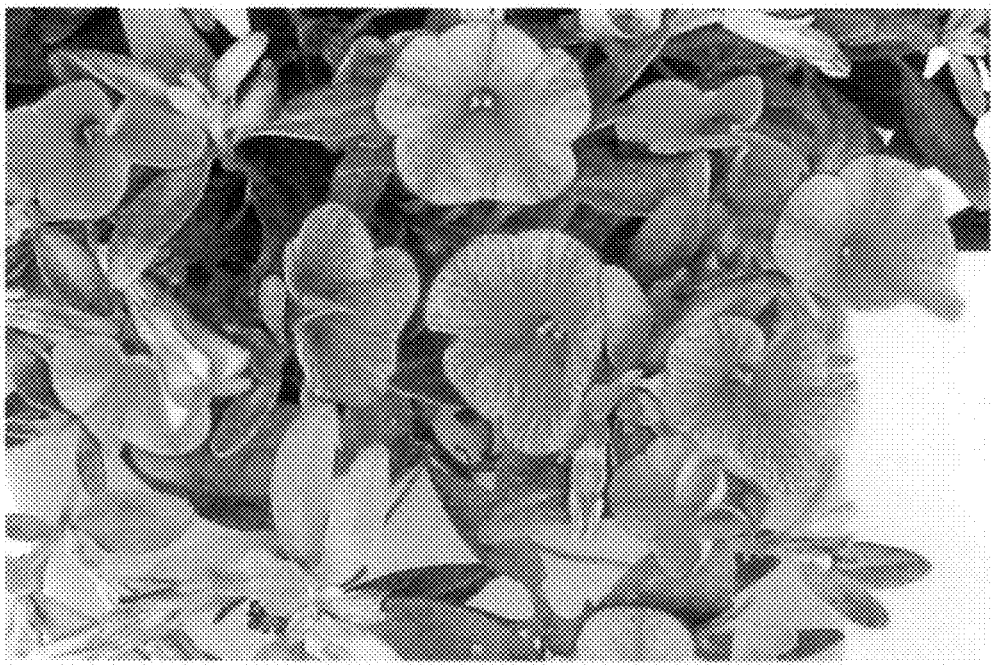
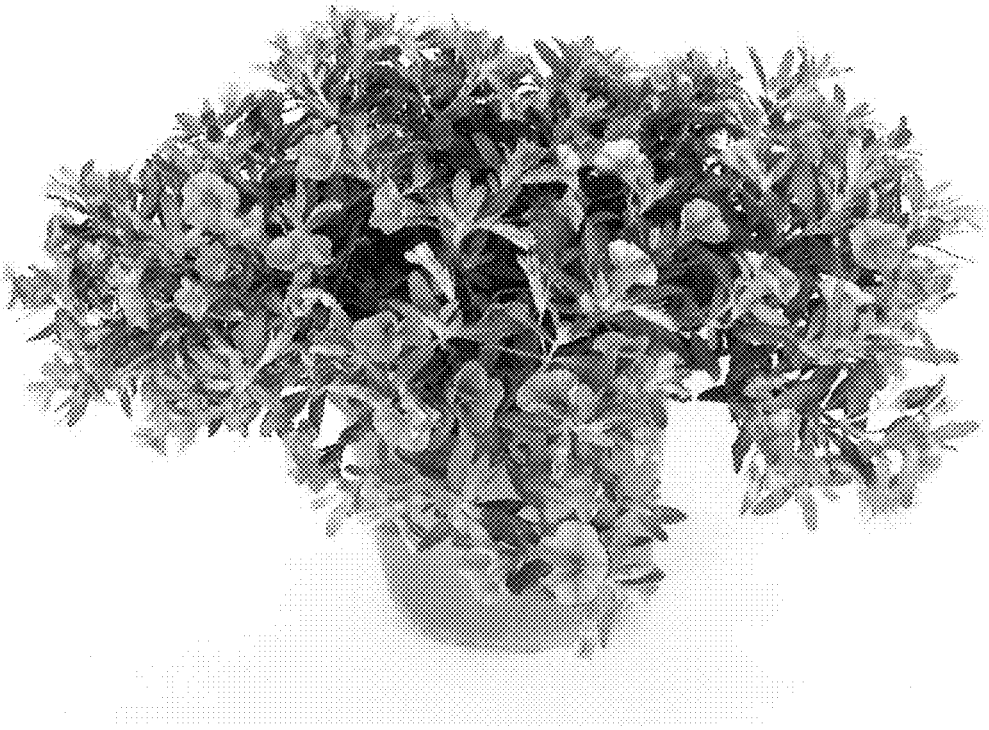

* * * * *